United States Patent [19]

Bömches et al.

[11] Patent Number: 4,579,855

[45] Date of Patent: Apr. 1, 1986

[54] MELFLOQUIN HYDROCHLORIDE

[75] Inventors: Helmut Bömches, Aesch; Bruno Hardegger, Riehen, both of Switzerland

[73] Assignee: Hoffmann-La Roche Inc., Nutley, N.J.

[21] Appl. No.: 655,813

[22] Filed: Oct. 1, 1984

[30] Foreign Application Priority Data

Oct. 7, 1983 [CH] Switzerland .......................... 5459/83

[51] Int. Cl.$^4$ .................... C07D 215/14; A61K 31/47
[52] U.S. Cl. .................................. 514/314; 546/152; 546/176
[58] Field of Search ................. 424/258; 546/152, 176

[56] References Cited

U.S. PATENT DOCUMENTS 4,327,215 4/1982 Hickmann ........................... 546/176
4,429,130 1/1984 Hickmann ........................... 546/167

FOREIGN PATENT DOCUMENTS 92185 10/1983 European Pat. Off. .

*Primary Examiner*—Donald G. Daus
*Assistant Examiner*—Robert Benson
*Attorney, Agent, or Firm*—Jon S. Saxe; Bernard S. Leon; William G. Isgro

[57] ABSTRACT

Mefloquin hydrochloride in the form of modification E as characterized by IR spectrum and X-ray diffraction pattern, as well as a process for the preparation thereof by treating mefloquin hydrochloride, comprising at least partially another modification, that is, mefloquin hydrochloride which is not pure mefloquin hydrochloride in the form of modification E, with methanol and/or ethanol, in the presence of less than 30 volume/percent of water.

6 Claims, 6 Drawing Figures

FIG. 1: Mefloquin hydrochloride, Modification A

FIG. 2: Mefloquin hydrochloride, Modification B

FIG. 3. Mefloquin hydrochloride, Modification C

FIG. 4: Mefloquin hydrochloride, Modification D

FIG. 5: Mefloquin hydrochloride, Modification E

X-ray diffraction diagram of mefloquin hydrochloride, modification E

Measured d-values

| Line No. | d (Å) | Line No. | d (Å) |
|---|---|---|---|
| 1 | 18.99 | 15 | 3.81 |
| 2 | 13.28 | 16 | 3.74 |
| 3 | 9.93 | 17 | 3.70 |
| 4 | 9.50 | 18 | 3.60 |
| 5 | 9.35 | 19 | 3.57 |
| 6 | 6.84 | 20 | 3.37 |
| 7 | 6.70 | 21 | 3.34 |
| 8 | 5.98 | 22 | 3.18 |
| 9 | 5.05 | 23 | 3.05 |
| 10 | 4.94 | 24 | 2.93 |
| 11 | 4.41 | 25 | 2.86 |
| 12 | 4.21 | 26 | 1.91 |
| 13 | 3.95 | 27 | 1.90 |
| 14 | 3.84 | 28 | 1.78 |

MELFLOQUIN HYDROCHLORIDE

BRIEF SUMMARY OF THE INVENTION

A process for the preparation of pure erythro-α-2-piperidyl-2,8-bis-(trifluoromethyl)-4-quinoline methanol hydrochloride in the form of its modification E, which comprises treating erythro-α-2-piperidyl-2,8-bis(trifluoromethyl)-4-quinolinemethanol hydrochloride produced, for example, by the catalytic hydrogenation of 2-pyridyl-2,8-bis(trifluoromethyl)-4-quinolyl ketone with methanol and/or ethanol containing less than 30 volume/percent of water and recovering pure erythro-α-2-piperidyl-2,8-bis-(trifluoromethyl)-4-quinolinemethanol hydrochloride in the form of modification E.

DETAILED DESCRIPTION OF THE INVENTION

Mefloquin hydrochloride, erythro-α-2-piperidyl-2,8-bis-(trifluoromethyl)-4-quinolinemethanol hydrochloride, is a valuable active substance for the treatment of the chloroquine-resistant form of malaria. In the processes for the preparation of mefloquin in which the last step consists in catalytically hydrogenating 2-pyridyl 2,8-bis-(trifluoromethyl)-4-quinolyl ketone there is always obtained in addition to the biologically active erythro form a smaller amount (about 5-15%) of the inactive and therefore undesired threo form.

The separation of the threo form from the erythro form and the purification of the latter can be achieved by treating the mixture of erythro- and threo-α-2-piperidyl-2,8-bis-(trifluoromethyl)-4-quinolinemethanol hydrochloride obtained by the hydrogenation with aqueous methanol or ethanol, about 60 to 95 volume/percent of water, whereby the threo form passes into solution and the erythro form remains behind. In a second step, residues of the threo compound as well as other by-products can be removed by further purification, for example by treatment with acetone, that is, via an acetone complex.

Figure 1:
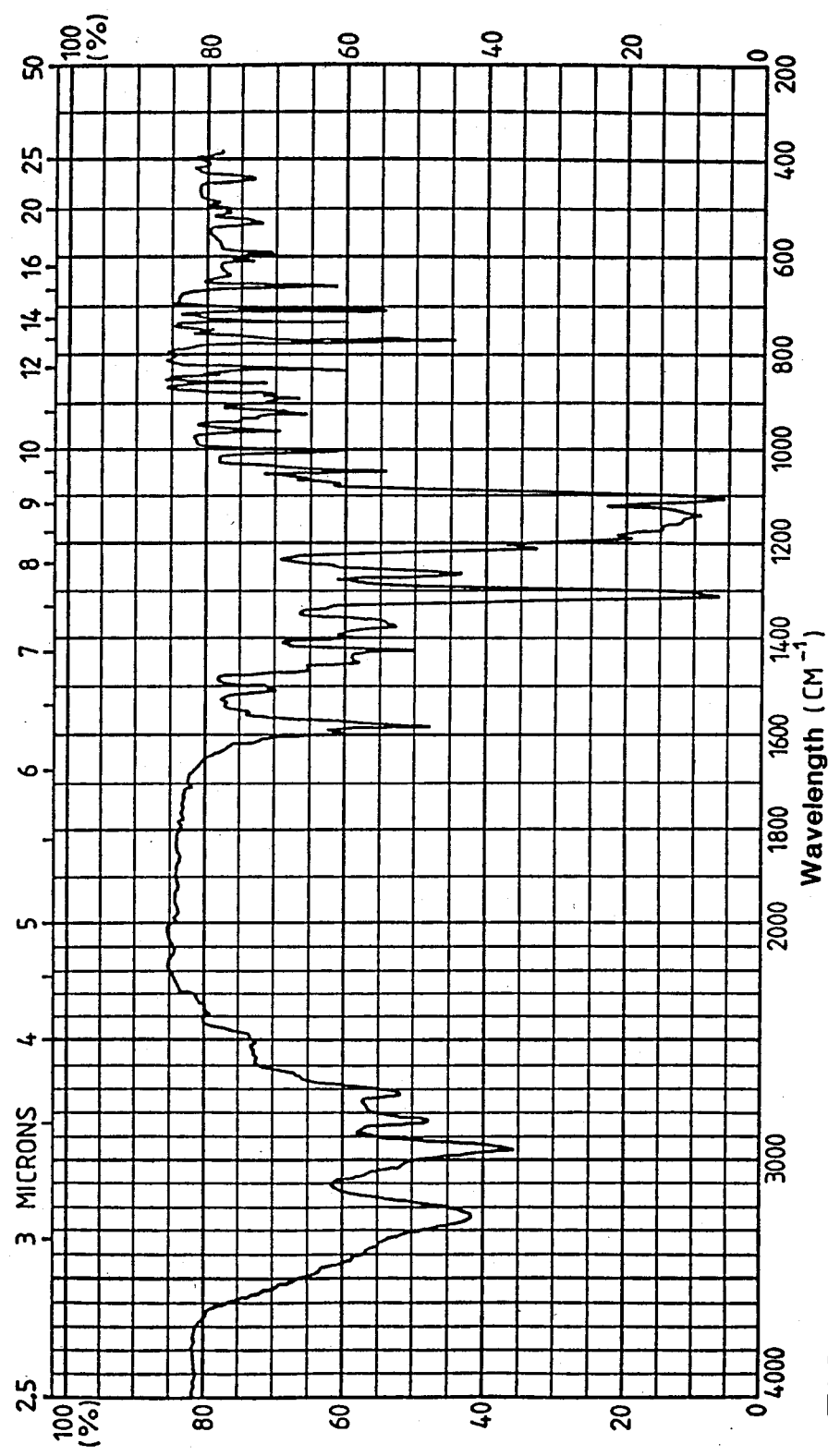
Figure 2:
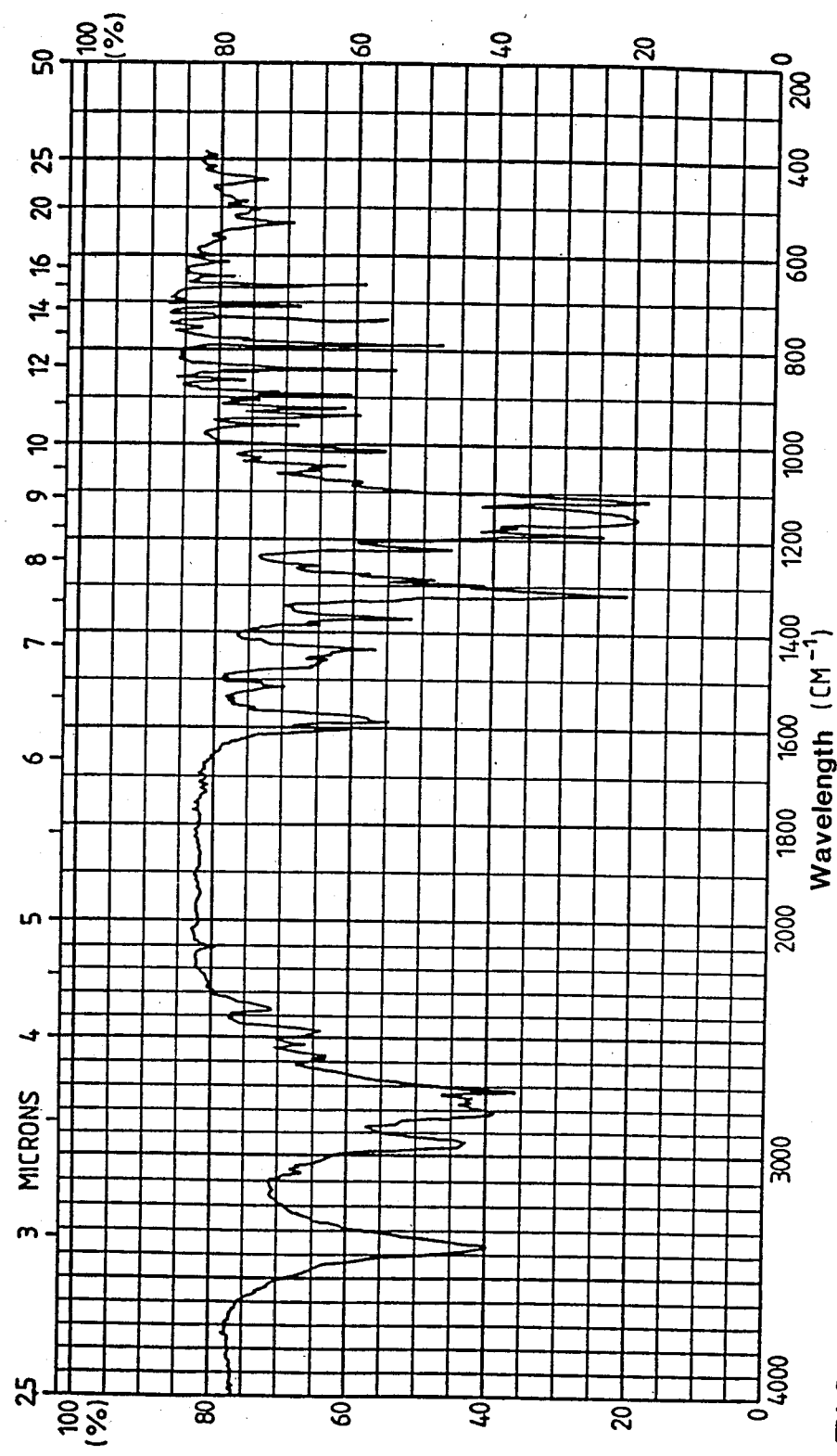
Figure 3:
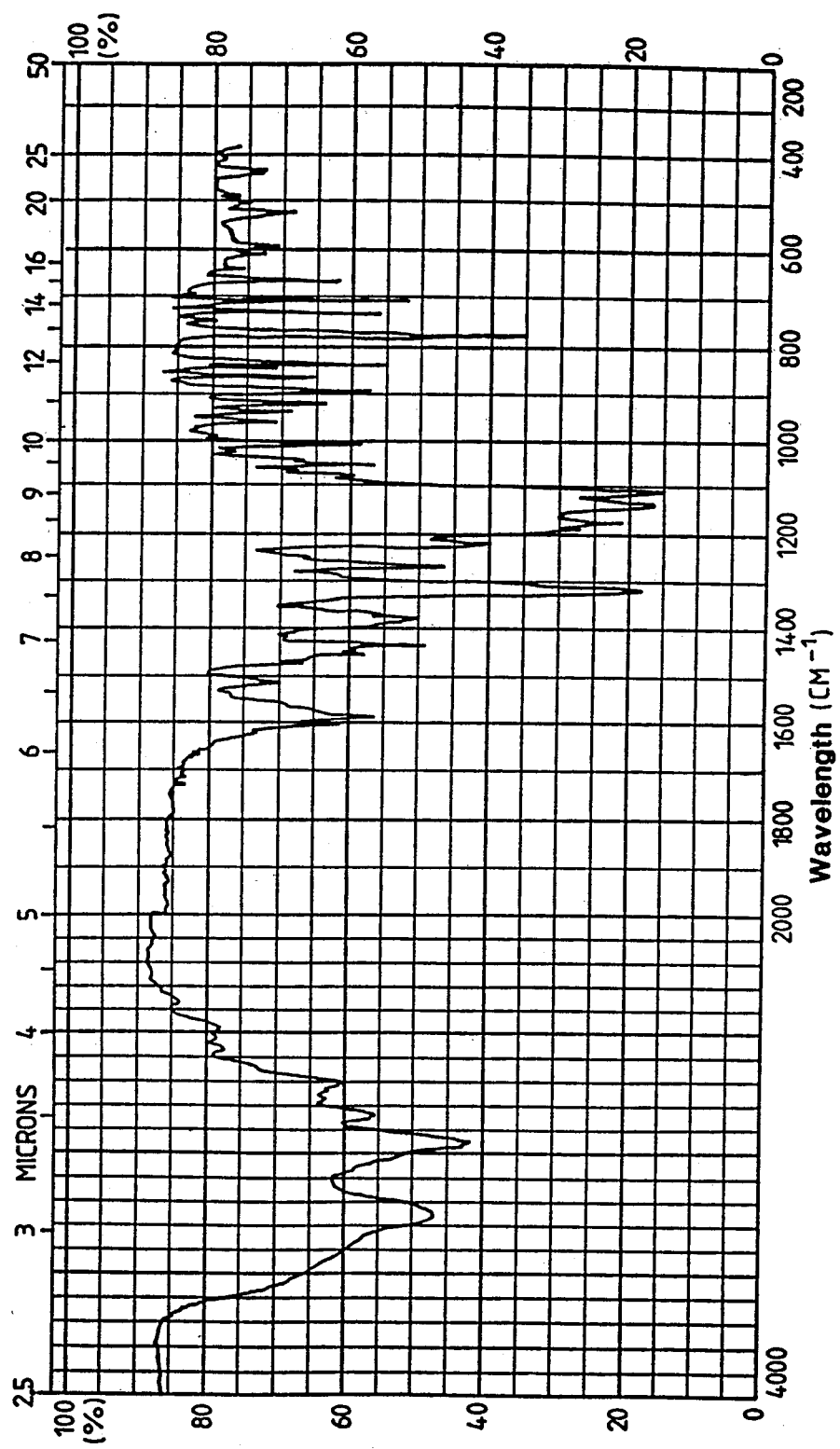
Figure 4:
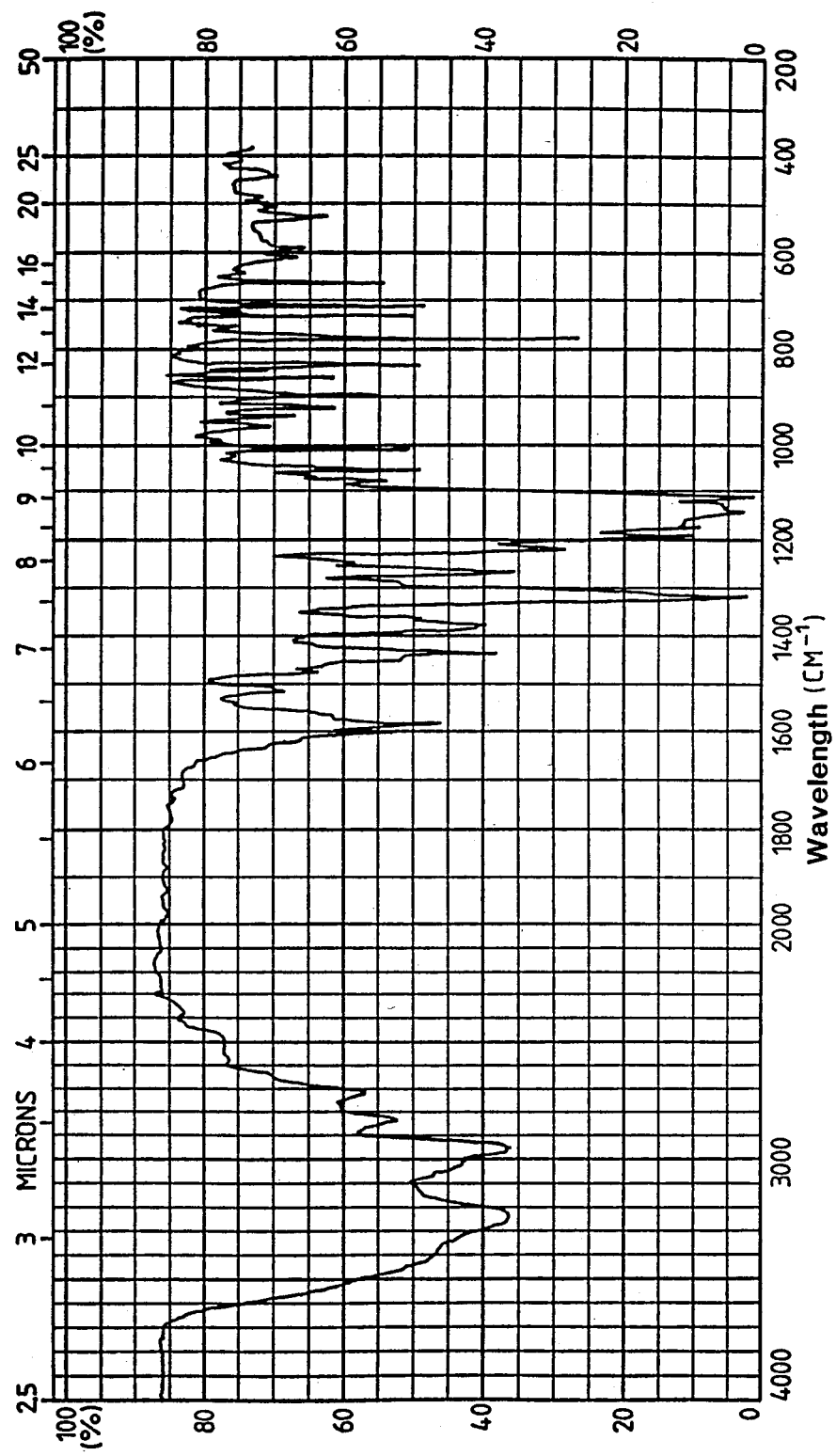

In this connection, it has been established that pure mefloquin hydrochloride occurs in various modifications which can differ from one another crystallographically or on the basis of their IR spectra. Thus, in the purification by means of acetonitrile there is obtained a modification A, mefloquin HCl, which is characterized by the IR spectrum A set out in FIG. 1, while in the case of brief treatment with acetone there is obtained modification B, mefloquin HCl acetone, and with water/alcohol mixtures there is obtained modification C, mefloquin HCl ½ H$_2$O, see IR spectra B and C, FIGS. 2 and 3, respectively. In the case of longer treatment of mefloquin hydrochloride with alcohol/water mixtures, about 50 to 80 volume/percent of water, there forms the modification D, mefloquin HCl ½ H$_2$O, which is the thermodynamically most stable modification, see IR spectrum D. FIG. 4.

It has now been found that by treatment with methanol and/or ethanol containing less than 30 volume/percent of water mefloquin hydrochloride is converted into polymorphic modification E which has particularly interesting properties.

Thus, tablets which contain mefloquin hydrochloride in the form of modification E have a better solubility and bioavailability than those which contain mefloquin hydrochloride in the form of modification D, which as already mentioned is the thermodynamically most stable modification.

Figure 5:
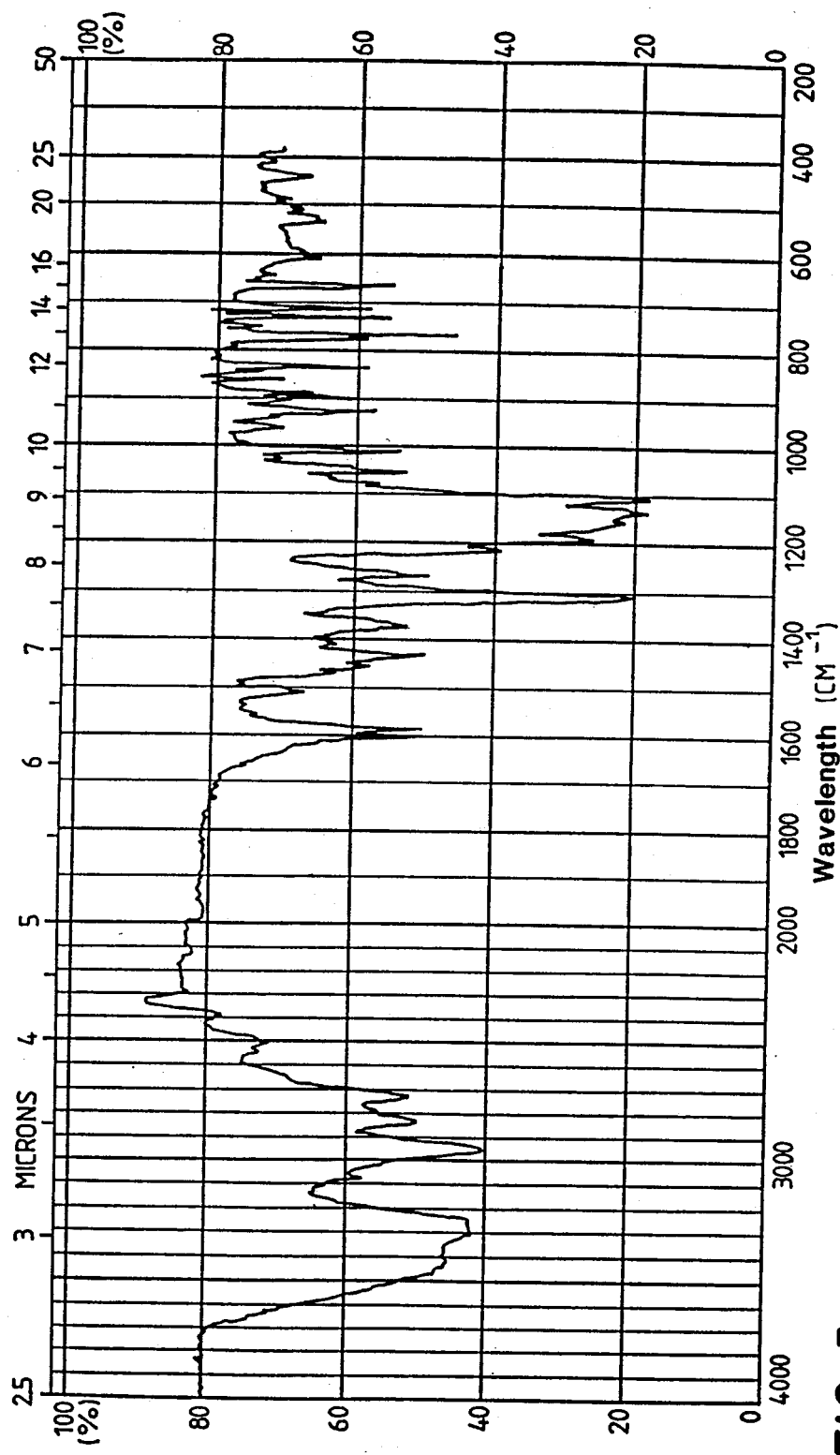

The IR spectrum characteristic for modification E is given in FIG. 5. A comparison of the IR spectra shows that the differences between modification E and modifications A to D are apparent mainly in the wavelength range 1100–1240 cm$^{-1}$.

Figure 6:

Modification E is also characterized by the X-ray diffraction pattern in accordance with FIG. 6, whereby not only the position but also the relative intensities of the lines are characteristic for the present crystal lattice and its composition.

Finally, modification E can also be characterized by d-values measured on the basis of the X-ray diffraction Pattern in accordance with FIG. 6. The d-value can be obtained by means of the Bragg's equation:

$$d = \frac{\lambda}{2 \sin \theta}$$

$\lambda$ = Wavelength of the X-rays
$\theta$ = Diffraction angle (in FIG. 6 4 mm correspond to a diffraction angle of 1°)

The results are given in FIG. 6.

The invention relates to mefloquin hydrochloride in the form of its modification E characterized by the IR spectrum in accordance with FIG. 5 and/or the X-ray diffraction pattern as shown in FIG. 6 and/or the D-values measured on the basis of this X-ray diffraction pattern.

Further, the present invention relates to a process for the preparation of pure mefloquin hydrochloride in the form of its modification E, which process comprises treating mefloquin hydrochloride, which is present at least partially in another modification, with methanol and/or ethanol, with no water present or optionally in the presence of less than 30 volume/percent of water.

The preparation of the modification E according to the process provided by the invention is preferably carried out at room temperature, and treatment for a few minutes is usually quite sufficient. It is, however, preferable to continue the treatment for at least a half hour.

In addition to methanol or ethanol or a mixture of methanol and ethanol, there can be present less than 30 volume/percent of water, preferably less than 10 volume/percent of water. It is especially preferred to use methanol and ethanol in pure form, without the addition of water.

The mefloquin hydrochloride which is present at least partially in another modification than the modification E, used as the starting material can be prepared by treating erythro-/threo-α-2-piperidyl-2,8-bis-(trifluoromethyl)-4-quinolinemethanol mixtures with aqueous methanol or ethanol, whereby the threo form passes into solution. The treatment can be carried out by stirring at room temperature for 30 minutes to several hours or while heating to about 80° C. and subsequently cooling to about 5° C. (in order to increase the yield). The water content of the solvent mixture can be varied in wide limits and conveniently lies at 60–95 volume/percent, preferably between 70 and 90 volume/percent. In the working-up of methanolic reaction solutions as are obtained, for example, in the catalytic hydrogenation of 2-pyridyl 2,8-bis-(trifluoromethyl)-4-quinolyl ketone in methanol containing hydrochloric acid, a portion of the methanol is conveniently firstly removed and then a corresponding amount of water is added. The thus-obtained mefloquin hydrochloride, crude material, which is conveniently washed with cold water and subsequently dried, is then practically free from the undesired threo form and is suitable as the starting material for the process provided by the invention.

This crude material is practically chemically uniform, but is present neither in a uniform crystal form nor in the thermodynamically most stable form, modification D, preferred as the starting material in the present process. Modification D can be produced by stirring the crude material for a longer time, that is, at least about 6 hours to about 12 hours, with an alcohol, for example, methanol, ethanol, isopropanol, but preferably methanol, in the presence of water, about 50–80 volume/percent. The treatment can be carried out at room temperature or, in order to increase the yield, while cooling to temperatures somewhat above 0° C. Modifications A to C can, of course, also be used as the starting material.

Medicaments containing mefloquin hydrochloride in its modification E are also an object of the present invention. In addition to pharmaceutically acceptable carrier materials, they can also contain other therapeutically valuable substances such as, for example, sulfadoxine and pyrimethamine. A tablet containing 250 mg of mefloquin hydrochloride in its modification E, 500 mg of sulfadoxine and 25 mg of pyrimethamine is a particularly valuable antimalarial agent.

The medicaments provided by the invention, which preferably contain in relation to mefloquin hydrochloride in the form of its modification E less than 10% of mefloquin hydrochloride in another form, can be used as pharmaceutical preparations with direct or delayed liberation of the active substance in admixture with an organic or inorganic inert carrier material which is suitable for oral administration such as, for example, water, gelatin, gum arabic, lactose, starch, magnesium stearate, talc, vegetable oils, polyalkylene glycols, and the like. The pharmaceutical preparations are preferably present in solid form, for example, as tablets, dragees, capsules. If desired, they are sterilized and/or contain further adjuvants such as preserving agents, stabilizing agents, wetting agents or emulsifying agents, flavor-improving agents, salts for varying the osmotic pressure or buffer substances. The pharmaceutical preparations can be prepared in a manner which is familiar to any person of ordinary skill in the art.

A preferred dosage unit for mefloquin hydrochloride in the form of the modification E is in the range of from about 1 to about 15 mg/kg.

The pharmaceutical preparations provided by the invention are suitable for the curative treatment of malaria, all forms, with a single dosage in the form of, for example, one or more tablets preferably containing 250 mg of mefloquin, depending on the body weight of the patient and the directions of the physician, as well as for the prophylaxis and suppressive therapy at intervals of 1–4 weeks.

The example which follow further illustrate the invention. All temperatures are in degrees centigrade unless otherwise stated.

EXAMPLE 1

1.5 g of mefloquin hydrochloride, in the form of modification D, were suspended in 5 ml of pure ethanol and equalibrated at 25° C. for 30 minutes in a vibration mixer. After centrifuging and removing the supernatant solution with a pipette, the residue was dried at room temperature in a vacuum dryer for two hours. Mefloquin hydrochloride was obtained in the form of its modification E.

EXAMPLE 2

1.5 g of mefloquin hydrochloride, in the form of modification D, were suspended in 5 ml of pure methanol and equilibrated at 25° C. for 30 minutes in a vibration mixer. After centrifuging and removing the supernatant solution with a pipette, the residue was dried at room temperature in a vacuum dryer for two hours. Mefloquin hydrochloride was obtained in the form of its modification E.

EXAMPLE 3

1.5 g of mefloquin hydrochloride, in the form of modification D, were suspended in 5 ml of various ethanol/water mixtures and equilibrated at 25° C. for 30 minutes, 24 hours or 72 hours, in a vibration mixer. After centrifuging and removing the supernatant solution with a pipette, the residue was dried at room temperature for two hours in a vacuum dryer. As is evident from Table 1 hereinafter, mefloquin hydrochloride was obtained in the form of its modification E, the equilibration time depending on the water content in the solvent mixture.

TABLE

| Solvent Ethanol:water | Crystallographical form of mefloquin hydrochloride | | |
|---|---|---|---|
|  | After 30 min | After 24 hrs. | After 72 hrs. |
| 70:30 | mod. D | mod. E | mod. E |
| 90:10 | mod. D + E | mod. E | mod. E |
| 92:8 | mod. D + E | mod. E | mod. E |
| 95:5 | mod. E | mod. E | mod. E |

EXAMPLE 4

1.5 g of mefloquin hydrochloride, in the form of modification A, were suspended in 5 ml of pure ethanol and equilibrated at 25° C. for 30 minutes in a vibration mixer. After centrifuging and removing the supernatant solution with a pipette, the residue was dried at room temperature in a vacuum dryer for two hours. Mefloquin hydrochloride was obtained in the form of its modification E.

EXAMPLE 5

1.5 g of mefloquin hydrochloride, in the form of modification C, were suspended in 5 ml of pure ethanol and equilibrated at 25° C. for 30 minutes in a vibration mixer. After centrifuging and removing the supernatant solution with a pipette, the residue was dried at room temperature in a vacuum dryer for two hours. Mefloquin hydrochloride was obtained in the form of its modification E.

EXAMPLE 6

| Tablets containing: | |
|---|---|
| Mefloquin hydrochloride modification (E) | 274.12 mg (corresponding to 250 mg of mefloquin) |
| Poloxalkol | 2.94 mg |
| Microcrystalline cellulose | 63.02 mg |
| Crosspovidone | 40.0 mg |
| Ammonium calcium alginate | 11.76 mg |
| Maize starch | 28.88 mg |
| Lactose | 50.58 mg |
| Talc | 11.0 mg |

| -continued |  |
| --- | --- |
| Tablets containing: |  |
| Magnesium stearate | 11.0 mg |
|  | 493.3 mg |

Mefloquin hydrochloride, in the form of modification D, is moistened with a solution of poloxalkol in alcohol and kneaded; it is then dried and sieved. There is obtained a granulate containing mefloquin hydrochloride in the form of modification E.

The granulate is mixed with microcrystalline cellulose, lactose, maize starch, Crosspovidone (portion) as well as ammonium calcium alginate. The powder mixture is moistened with a water/alcohol mixture and kneaded. It is then granulated, dried and sieved.

To the granulate obtained are added Crosspovidone (2nd portion) as well as a sieved mixture of the talc and the magnesium stearate; all powder ingredients are mixed with one another and the resulting mixture is pressed to tablets of appropriate size.

EXAMPLE 7

| Tablets containing: |  |
| --- | --- |
| Mefloquin hydrochloride, modification (E) | 274.12 mg (corresponding to 250 mg of mefloquin) |
| Sulfadoxine | 500.0 mg |
| Pyrimethamine | 25.0 mg |
| Dioctyl sodium sulfosuccinate | 1.0 mg |
| Methylcellulose | 7.5 mg |
| Sodium carboxymethyl starch | 35.0 mg |
| Microcrystalline cellulose | 48.38 mg |
| Magnesium stearate | 9.0 mg |
|  | 900.0 mg |

Mefloquin hydrochloride, in the form of modification D, is moistened with alcohol and kneaded; it is then dried and sieved. There is obtained a granulate containing mefloquin hydrochloride in the modification E.

Sulfadoxine, pyrimethamine, sodium carboxymethyl starch and the granulate of mefloquin hydrochloride are worked into an aqueous solution of dioctyl sodium sulfosuccinate and methylcellulose and the mixture obtained is kneaded. It is then granulated, dried and sieved.

Sieved microcrystalline cellulose and sieved magnesium stearate are added to the granulate; all powder ingredients are mixed with one another and the mixture obtained is pressed to tablets.

We claim:

1. Essentially pure erythro-$\alpha$-2-piperidyl-2,8-bis-(trifluoromethyl)-4-quinolinemethanol hydrochloride in the form of its modification E.

2. Essentially pure erythro-$\alpha$-2-piperidyl-2,8-bis-(trifluoromethyl)-4-quinolinemethanol hydrochloride in the form of its modification E characterized by the IR spectrum, FIG. 5, and/or the X-ray diffraction pattern and/or the d-values, FIG. 6.

3. A non-liquid, dry pharmaceutical composition comprising an antimalarially effective amount of essentially pure mefloquin hydrochloride in the form of its modification E and an inert carrier material.

4. A non-liquid, dry pharmaceutical composition, in accordance with claim 3, which contains pyrimethamine and sulfadoxine in addition to the essentially pure mefloquin hydrochloride in the form of its modification E in an antimalarially effective amount.

5. A method of treating or preventing all forms of malaria in a host in need of such treatment which comprises administering to said host a pharmaceutical composition containing an antimalarially effective amount of essentially pure mefloquin hydrochloride in the form of its modification E alone or in combination with other therapeutically active substances.

6. A method of treating or preventing all forms of malaria in a host in need of such treatment which comprises administering to said host a pharmaceutical composition containing an antimalarially effective amount of a combination of essentially pure mefloquin hydrochloride in the form of its modification E, sulfadoxine and pyrimethamine.

* * * * *